United States Patent
Hirose et al.

(10) Patent No.: US 7,786,093 B2
(45) Date of Patent: Aug. 31, 2010

(54) ANTISTRESS AGENT

(75) Inventors: Yoshitaka Hirose, Itami (JP); Shinji Murosaki, Nara (JP); Yoshihiro Yamamoto, Itami (JP); Norio Yamamoto, Kobe (JP); Koutarou Muroyama, Nishinomiya (JP); Takuya Sato, Kobe (JP)

(73) Assignee: Health Wellness Foods Corporation, Hyogo (JP)

( * ) Notice: Subject to any disclaimer, the term of this patent is extended or adjusted under 35 U.S.C. 154(b) by 0 days.

(21) Appl. No.: 11/631,618

(22) PCT Filed: Mar. 7, 2005

(86) PCT No.: PCT/JP2005/003907

§ 371 (c)(1),
(2), (4) Date: Mar. 2, 2007

(87) PCT Pub. No.: WO2006/006267

PCT Pub. Date: Jan. 19, 2006

(65) Prior Publication Data

US 2007/0203093 A1    Aug. 30, 2007

(30) Foreign Application Priority Data

Jul. 7, 2004    (JP) .............................. 2004-201158

(51) Int. Cl.
*A61K 31/7012* (2006.01)
(52) U.S. Cl. ........................................................ 514/53
(58) Field of Classification Search ........................ None
See application file for complete search history.

(56) References Cited

U.S. PATENT DOCUMENTS

| 2003/0153514 A1* | 8/2003 | Yagita ........................... 514/26 |
| 2009/0169643 A1* | 7/2009 | Koyama et al. .............. 424/641 |

FOREIGN PATENT DOCUMENTS

| JP | 9-52834 | 2/1997 |
| JP | 11-228425 | 8/1999 |
| JP | 2001-64174 | 3/2001 |
| JP | 2002-80364 | 3/2002 |
| JP | 2002-265366 | 9/2002 |
| JP | 2002-265385 | 9/2002 |
| JP | 2002-325555 | 11/2002 |

OTHER PUBLICATIONS

Padgett et al. How stress influences the immune response, Trends in Immunology, vol. 24 No.* Aug. 2008 p. 444-448.*
Shinji et al., Yakuri to Chiro, 2001, abstract, vol. 29, No. 11, pp. 815-825.*
Hirose et al., Immunopharmacology and Immunotoxicology, vol. 26, No. 3, pp. 387-399, 2004.*
Murosaki, S. et al., "Immunopotentiating Activity of Nigerooligosaccharides for the T Helper 1-Like Immune Response in Mice", *Biosci. Biotechnol. Biochem.*, 63(2): 373-378, 1999.
Murosaki, S. et al., "Effects of intake of nigerooligosaccharides-supplemented syrup on the immune function and quality of life in the healthy elderly", *Jpn. Pharmacol. Ther.*, 29(11): 815-826, 2001.
Murosaki, S. et al., "Effects of intake of nigerooligosaccharides-supplemented syrup on the immune function and quality of life in healthy young adult subjects", *Jpn. Pharmacol. Ther.*, 30(2): 81-90, 2002.
Murosaki, S. et al., "Nigerooligosaccharides augments natural killer activity of hepatic mononuclear cells in mice", *International Immunopharmacology*, 2: 151-159, 2002.
Hirose, Y. et al., "Nigerooligosaccharides Augments Mitogen-Induced Proliferation and Suppresses Activation-Induced Apoptosis of Human Peripheral Blood Mononuclear Cells", *Immunopharmacology and Immunotoxicology*, 26(3): 387-399, 2004.

* cited by examiner

*Primary Examiner*—Brian-Yong S Kwon
(74) *Attorney, Agent, or Firm*—Wenderoth, Lind & Ponack, L.L.P.

(57) ABSTRACT

The present invention relates to an antistress agent comprising as an active ingredient a saccharide containing 3-O-α-D-glucopyranosyl-D-glucose as a structural unit. It is an object of the present invention to provide said antistress agent which is free from side effects as a medicine, and can be taken habitually and also can be ingested simply as a food or a beverage, or the like.

7 Claims, No Drawings

ANTISTRESS AGENT

This application is a U.S. national stage of International Application No. PCT/JP2005/003907 filed Mar. 7, 2005.

TECHNICAL FIELD

The present invention relates to an antistress agent which comprises as an active ingredient a saccharide, especially a saccharide containing 3-O-α-D-glucopyranosyl-D-glucose as a structural unit.

BACKGROUND ART

Any human or animal is under not a few stresses, and these stresses exert great effects not only on the nervous system, but also on the immune system via the nervous system. In general, under stress-loaded states, a hormone such as a glucocorticoid or the like which is secreted from the adrenal gland is secreted as an antistress hormone to direct an action to heighten vigor and the like. However, on the other hand, it has been known that the glucocorticoid reduces the growth ability or the function of immunocompetent cells and also acts disadvantageously on the living body by inducing apoptosis of the immunocompetent cells, accelerating degradation of proteins, inhibiting their synthesis, and the like (see for example, non-patent literature 1 and non-patent literature 2). Therefore, if the stress states persist and become chronic, the glucocorticoid is secreted continuously to induce a variety of symptoms caused by the action of glucocorticoids, which is disadvantageous to the living body, for example, the so-called secondary problematic symptoms due to chronic stress(es), such as decrease in infection-defense ability, delay of wound healing, metabolic disorders, and the like.

Against the stress(es), drugs such as antianxiety drugs, sleeping drugs, and the like are considered to be an effective means alleviating temporarily the reaction of body and mind when exposed to the stress(es). However, there has not been known any antistress drugs that are free from side effects and can be taken habitually and continuously. For example, although a benzodiazepine drug which is a representative antianxiety drug, is said to alleviate anxiety, tension, depression and muscle tonus without affecting the level of consciousness, it has been known that a high-dose administration or a repetitive administration of the drug causes abstinence symptoms, such as convulsion, delirium, and the like, as well as side effects, such as sleepiness, stagger, dizziness, hepatopathy, leucopenia, and the like. Also, a variety of tablets or drinks are commercially available as an object of an analeptic or a refresher of the body, but any effect against the stress(es) is/are not distinct at present.

On the other hand, a composition which comprises as an active ingredient a saccharide containing 3-O-α-D-glucopyranosyl-D-glucose as a structural unit has been known to have the actions of immunostimulants (patent literature 1), NK cell activators (patent literature 2), QOL improvers (patent literature 3), foods or beverages to suppress reduction in the immune function due to nutritional disorders (patent literature 4), and the like. However, these literatures do not describe at all that the above-mentioned saccharide has an antistress action, and improve or suppress symptoms associated with reduction in function of immunocompetent cells or apoptosis of the immunocompetent cells occurring under the influence of the glucocorticoids especially due to chronic stress(es), and the like. As stated above, although the above-mentioned saccharides have been known to stimulate the immune system, it has not been known at all how the saccharide acts against the stress(es), especially against a variety of symptoms associated with chronic stress(es).

Patent literature 1: Japanese Patent No. 3396129
Patent literature 2: Japanese Patent Application Laid-Open No. 2002-265366
Patent literature 3: Japanese Patent Application Laid-Open No. 2002-265385
Patent literature 4: Japanese Patent Application Laid-Open No. 2002-325555
Non-patent literature 1: Tomio Tada, "Immunology Illustrated," p 178, Nankodo, 2000
Non-patent literature 2: Katsuiku Hirokawa, "Cross Talk on Nerve, Internal Secretion and Immunity," p 177-185, Japan Scientific Societies Press, 1993

DISCLOSURE OF THE INVENTION

Problems to be Solved by the Invention

It is an object of the present invention to provide an antistress agent which, when used as a medicine, is free from side effects, can be taken habitually, and can also be simply ingested as a food or a beverage, or the like. In more detail, it is an object to provide an antistress agent which suppress or prevent a variety of symptoms associated with chronic stress(es).

MEANS FOR SOLVING THE PROBLEMS

In order to solve the above-mentioned problems, the present inventors have carried out intensive investigations by using as indicators a variety of actions of glucocorticoids which are secreted at the time of the stress(es). Dexamethasone was used as the glucocorticoid. Dexamethasone is a synthetic glucocorticoid, whereas brings about disadvantages for the living body, such as suppression of the growth or reduction of the function of immunocompetent cells, suppression of cytokine production by immunocompetent cells and apoptosis induction, and the like in a similar manner to those of biological glucocorticoids, such as cortisol, corticosterone, cortisone, and the like, which are secreted in the living body in response to the stress(es). For example, it was found in an in vitro test using human mononuclear cells comprising immunocompetent cells such as T cells, B cells and the like that saccharides containing 3-O-α-D-glucopyranosyl-D-glucose as a structural unit suppress decrease in cell growth of human mononuclear cells and decrease in cytokine production due to dexamethasone as well as apoptosis of human mononuclear cells. Moreover, it was found in an in vivo test that saccharides containing 3-O-α-D-glucopyranosyl-D-glucose as a structural unit suppresses atrophy of the thymus gland and spleen of the immunocompetent organs due to dexamethasone, and also suppress decrease in cytokine productivity. On the basis of these findings, the present inventors have further made extensive studies, and accomplished the present invention.

Namely, the present invention relates to:

(1) an antistress agent comprising as an active ingredient a saccharide containing 3-O-α-D-glucopyranosyl-D-glucose as a structural unit;

(2) the antistress agent according to the above (1), which is a suppressor against reduction of immune function due to stress;

(3) the antistress agent according to the above (1), which is a suppressor against decrease in cell growth of immunocompetent cells due to stress;

(4) the antistress agent according to the above (1), which is a suppressor against decrease in cytokine production due to stress;

(5) the antistress agent according to the above (1), which is a suppressor of apoptosis of immunocompetent cells due to stress;

(6) the antistress agent according to the above (1), which is an agent for improving and/or preventing a secondary symptom due to chronic stress;

(7) the antistress agent according to the above (6), wherein the secondary symptom due to chronic stress is caused by a glucocorticoid;

(8) the antistress agent according to any one of the above (1) to (7), wherein the saccharide is a nigerooligosaccharide;

(9) the antistress agent according to the above (8), wherein the nigerooligosaccharide is at least one kind of saccharides selected from the group consisting of nigerose, nigerosylglucose and nigerosylmaltose; and

(10) the antistress agent according to any one of the above (1) to (9), which is a food or a beverage.

Also, the present invention relates to:

(11) a method for prevention or therapy of stress, which comprises subjecting a mammal to administration or ingestion, or eating or drinking of an effective amount of a saccharide containing 3-O-α-D-glucopyranosyl-D-glucose as a structural unit;

(12) a method for prevention or therapy of reduction of immune function due to stress, which comprises subjecting a mammal to administration or ingestion, or eating or drinking of an effective amount of a saccharide containing 3-O-α-D-glucopyranosyl-D-glucose as a structural unit;

(13) a method for prevention or therapy of stress, which comprises subjecting a mammal to administration or ingestion, or eating or drinking of an effective amount of a saccharide containing 3-O-α-D-glucopyranosyl-D-glucose as a structural unit;

(14) a method for prevention or therapy of decrease in cytokine production due to stress, which comprises subjecting a mammal to administration or ingestion, or eating or drinking of an effective amount of a saccharide containing 3-O-α-D-glucopyranosyl-D-glucose as a structural unit;

(15) a method for prevention or therapy of apoptosis of immunocompetent cells due to stress, which comprises subjecting a mammal to administration or ingestion, or eating or drinking of an effective amount of a saccharide containing 3-O-α-D-glucopyranosyl-D-glucose as a structural unit;

(16) a method for prevention or therapy of a secondary symptom due to chronic stress, which comprises subjecting a mammal to administration or ingestion, or eating or drinking of an effective amount of a saccharide containing 3-O-α-D-glucopyranosyl-D-glucose as a structural unit;

(17) the method for prevention or therapy according to the above (16), wherein the secondary symptom due to chronic stress is caused by a glucocorticoid;

(18) the method for prevention or therapy according to any one of the above (11) to (17), wherein the saccharide is a nigerooligosaccharide; and

(19) the method for prevention or therapy according to the above (18), wherein the nigerooligosaccharide is at least one kind of saccharides selected from the group consisting of nigerose, nigerosylglucose and nigerosylmaltose.

Furthermore, the present invention relates to:

(20) use of a saccharide containing 3-O-α-D-glucopyranosyl-D-glucose as a structural unit for producing a medicine, a food, or a beverage for prevention or therapy of stress;

(21) the use according to the above (20), wherein the prevention or therapy of stress is to suppress reduction of immune function due to stress;

(22) the use according to the above (20), wherein the prevention or therapy of stress is to suppress decrease in cell growth of immunocompetent cells due to stress;

(23) the use according to the above (20), wherein the prevention or therapy of stress is to suppress decrease in cytokine production due to stress;

(24) the use according to the above (20), wherein the prevention or therapy of stress is to suppress apoptosis of immunocompetent cells due to stress;

(25) the use according to the above (20), wherein the prevention or therapy of stress is to improve or prevent a secondary symptom due to chronic stress;

(26) the use according to the above (25), wherein the secondary symptom due to chronic stress is caused by a glucocorticoid;

(27) the use according to any one of the above (20) to (26), wherein the saccharide is a nigerooligosaccharide;

(28) the use according to the above (27), wherein the nigerooligosaccharide is at least one kind of saccharides selected from the group consisting of nigerose, nigerosylglucose and nigerosylmaltose; and

(29) a commercial package accommodating a composition comprising a saccharide containing 3-O-α-D-glucopyranosyl-D-glucose as a structural unit, wherein a label or an instruction indicating that the composition can or should be used as an antistress agent.

The stress(es) in the present invention refer(s) to stressors, for example, phenomena in biologically strained states that are caused by physical (high temperature and noise, etc.), chemical (adverse drug reaction, etc.), biological (diseases, injuries, etc.) and mental (troubles in human relations, etc.) factors, and the like. Also, the above-mentioned apoptosis refers to cell death characterized by a series of morphological changes that are regulated by a gene and occur mainly in the nucleus.

EFFECT OF THE INVENTION

The antistress agent of the present invention can be used for relaxation of temporary or chronic stress(es). The antistress agent of the present invention, when used as a medicine, is free from side effects and can be taken habitually, and can also be simply ingested as foods or beverages, or the like.

The antistress agent of the present invention can suppress, for example, reduction in the immune function or the like due to the stress(es). Especially, the antistress agent of the present invention can be preferably used in the case of chronic stress(es) where the stress(es) is/are sustained. The antistress agent of the present invention, when used in the case of the chronic stress(es), can suppress, for example, decrease in cytokine production, apoptosis of immunocompetent cells, atrophy of immunocompetent organs, and the like, which are caused, for example, by glucocorticoids (for example, cortisol, corticosterone, cortisone, etc.) which are continuously secreted in response to the chronic stress(es).

The antistress agent of the present invention can improve or prevent the action of the glucocorticoids secreted at the time of the chronic stress(es), which is disadvantageous to the living body, for example, reduction in infection-defense ability, delay of wound healing, metabolic disorders, or the like.

BEST MODE FOR CARRYING OUT THE INVENTION

The saccharide containing 3-O-α-D-glucopyranosyl-D-glucose as a structural unit used in the present invention includes, for example, an oligosaccharide comprising at least one or more α-1,3-glycosidic linkages with a glucose polymerization degree of not less than about 2, preferably an oligosaccharide having a glucose polymerization degree of about 2 to 10, more preferably a nigerooligosaccharide which is an oligosaccharide having a glucose polymerization degree of about 2 to 7, and these saccharides are preferably used in the present invention. Such nigerooligosaccharides encompass, besides an oligosaccharide comprising only α-1,3-glycosidic linkages, an oligosaccharide comprising α-1,3-glycosidic linkage(s) and another linkage(s) (for example, α-1,1-, α-1,2-, α-1,4-, or α-1,6-glycosidic linkage, etc.), and the like. In particular, it is more preferred in the present invention to use nigerose, nigerosylglucose, nigerosylmaltose or the like, which is represented by the following formula:

Academic Press (1962)), a method for producing nigerose by using the known glycosyl transfer/condensation reaction with α-glucosidase (Ken-ichi Kanaya et al., Nippon Nogeikagaku Kaishi, 53, 385-390 (1979), H. Fujimoto et al., Agric. Biol. Chem., 52, 1345-1351 (1988), etc.), a method for producing nigerose by treating a starch hydrolysate with a cyclodextrin synthase (Japanese Patent Application Laid-Open No. 3-22958), a method for producing nigerooligosaccharides by treating a substrate comprising a polysaccharide or oligosaccharide containing α-1,4-glycosidic linkage(es) with one or two or more kinds of glycosyltransferases yielding the α-1,3-glycosidic linkage(s), prepared specifically by cultivation of a fungus belonging to the genus *Acremonium* capable of producing the glycosyltransferase yielding the α-1,3-linkage(s), for example, *Acremonium* sp. S4G13 (FERM BP-4373), according to a conventional method (Japanese Patent Application Laid-Open No. 7-59559), and the like. The nigerooligosaccharide used in the present invention may be prepared by any one of the methods and they are not limited to the above methods. However, the method described in the above-mentioned Japanese Patent Application Laid-Open No. 7-59559 is considered to be the most economically

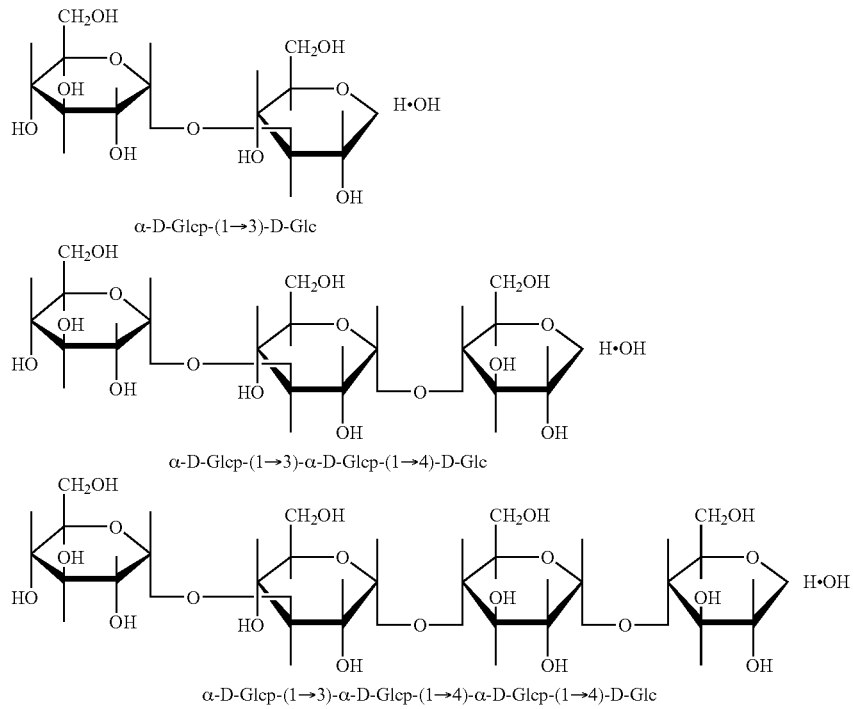

α-D-Glcp-(1→3)-D-Glc

α-D-Glcp-(1→3)-α-D-Glcp-(1→4)-D-Glc

α-D-Glcp-(1→3)-α-D-Glcp-(1→4)-α-D-Glcp-(1→4)-D-Glc

The above-mentioned saccharides may be used alone or may be used in two or more combinations thereof.

The saccharides containing 3-O-α-D-glucopyranosyl-D-glucose as a structural unit used in the present invention can be easily produced according to the known methods. Specifically, for example, preferable nigerooligosaccharide to be used in the present invention can be produced, for example, by a method for producing nigerooligosaccharides by hydrolysis of nigeran, elsinan or the like which is a polysaccharide produced by microorganisms and is served as a substrate, using an enzyme, an acid or the like (M. Stacey and J. M. Webber: Methods in Carbohydrate Chemistry, I, 339-341, excellent among the heretofore known methods, and it is also preferred in the present invention to use the nigerooligosaccharide prepared according to this method.

Also, the antistress agent of the present invention, when used as a medicine, may be produced in a variety of dosage forms. Since the antistress agent according to the present invention is free from side effects and can be taken habitually without any problems, it can be used not only as a medicine, but also as a food or a beverage. Specifically, it is also possible to provide the antistress agent according to the present invention as the food or beverage, for example, in the form of a nutritional supplementary food, a seasoning, a processed meat product, a processed marine product, a processed agricultural product, a staple, a seasoned food, a ready-to-eat food, a dessert, a milky oil product, a sweets, a snack, or the like.

The antistress agent according to the present invention is characterized by comprising a saccharide containing 3-O-α-D-glucopyranosyl-D-glucose as a structural unit, and may further contain an additional ingredient, for example, a per se known food or beverage, or a food or beverage ingredient, a pharmaceutical carrier or excipient, a food additive, or the like. Such additional ingredient is not particularly limited, but can be appropriately selected by a person skilled in the art depending on the specific usage of the objective medicine or food or beverage, whereas specifically, in the case of medicines, the ingredient includes an excipient (for example, fructose, D-sorbitol, glucose, carmellose, starch, crystalline cellulose, lactose, etc.), a disintegrant (for example, carmellose, starch, crystalline cellulose, low-substituted hydroxypropyl cellulose, etc.), a binder (for example, gum acacia, carmellose, gelatin, crystalline cellulose, simple syrup, honey, hydroxypropyl cellulose, povidone, methylcellulose, etc.), a surfactant (for example, polyoxyl 40 stearate, polysorbate 80, polyoxyethylene hydrogenated castor oil, etc.), an emulsifier (for example, polyoxyl 40 stearate, sorbitan sesquioleate, polysorbate 80, sodium lauryl sulfate, lauromacrogol, gum arabic, cholesterol, stearic acid, povidone, glyceryl monostearate, etc.), a plasticizer (for example, glycerin, propylene glycol, macrogol, etc.), a lubricant (for example, magnesium silicate, carmellose, light anhydrous silicic acid, stearic acid, calcium stearate, magnesium stearate, talc, etc.) and a saccharide (for example, white soft sugar, honey, simple syrup, glucose, etc.), a pH-adjusting agent (for example, hydrochloric acid, citric acid, sodium hydrogen carbonate, potassium hydroxide, sodium hydroxide, sodium carbonate, etc.), a preservative (for example, benzoic acid, benzalkonium chloride, ethyl parahydroxybenzoate, butyl parahydroxybenzoate, propyl parahydroxybenzoate, methyl parahydroxybenzoate, etc.), a flavor (for example, fennel oil, orange oil, cinnamon oil, thymol, orange peel tincture, dl-menthol, 1-menthol, eucalyptus oil, etc.), or a coloring agent (for example, Food Red No. 2, No. 3, No. 40, No. 102, No. 104, No. 105 or No. 106, Food Yellow No. 4 or No. 5, Food Green No. 3, Food Blue No. 1 or No. 2, titanium dioxide, sodium copper chlorophyllin, turmeric, gardenia, annatto dye, kaoliang dye, etc.) and the like, as well as, in the case of a food or a beverage, the ingredient includes a variety of nutrients (for example, saccharide, lipid, mineral (iron, calcium, magnesium, zinc, chromium, selenium, manganese, copper, iodine, etc.), a protein, an amino acid, etc.), a flavor, a coloring agent, an antioxidant (for example, ascorbic acid, sodium thiosulfate, tocopherol, sodium hydrogen sulfite) and the like, or a flavoring substance such as cheese, chocolate, and the like, a synthetic sweetener (for example, saccharin sodium, aspartame, acesulfame potassium, disodium glycyrrhizinate, etc.), and the like.

Furthermore, the antistress agent of the present invention, not otherwise contrary to the object of the present invention, may be used in combination with other antistress agents, including, for example, an antianxiety drug (for example, chlordiazepoxide, oxazolam, diazepam, etc.) and a hypnotic drug (for example, nitrazepam, estazolam, haloxazolam, etc.), or a vitamin (for example, vitamin A, vitamin $B_1$, vitamin $B_2$, vitamin $B_6$, niacinamide, pantothenic acid, vitamin $B_{12}$, vitamin E, biotin, vitamin C, etc.), and the like.

The antistress agent of the present invention can take a variety of dosage forms, depending on the method of ingestion and the route of ingestion, such as oral preparations (for example, syrup, powder, granule, pill, tablet, hard capsule, soft capsule, etc.), suppositories and injections, and the like, whereas it is preferred to use the oral preparation. Also, the antistress agent of the present invention, when used as a food or a beverage, can be provided in the form of granule, tablet, dragee, chewing gum, candy, jerry, drink or the like, where this form is not limited to the above-mentioned form.

The ingestion dose of the antistress agent of the present invention, although it alters depending on the sex, the age, the state of health, and the like of the ingesting people and it is therefore difficult to generally determine the dose, is desirably set in consideration of the absorption ratio in the case of the oral preparation, so as to take a daily ingestion dose of about 4 mg to about 40 g, preferably about 10 mg to about 20 g, more preferably about 50 mg to about 10 g, of a saccharide containing 3-O-α-D-glucopyranosyl-D-glucose as a structural unit, preferably a mixture of one or two or more kinds of nigerooligosaccharides selected from nigerose, nigerosylglucose and nigerosylmaltose. In the case of parenteral preparations such as injection, infusion fluid and the like, the ingestion dose is desirably set so as to administer a daily dose of about 5 mg to about 5 g, preferably about 25 mg to about 2.5 g, more preferably about 100 mg to about 1 g, of the active ingredient, preferably a mixture of one or two or more kinds of nigerooligosaccharides selected from nigerose, nigerosylglucose and nigerosylmaltose. Further, the ingestion frequency may be once a day or multiple times a day. Hereupon, the term "ingestion" used herein shall also include "administration".

Moreover, the present invention provides a method for prevention or therapy of stress(es) as well as a method for prevention or therapy of decrease in cytokine production due to stress(es), a method for prevention or therapy of apoptosis of immunocompetent cells due to stress(es), or a method for prevention or therapy of the secondary symptoms due to chronic stress(es), said these methods being characterized by subjecting a mammal to administration or ingestion, or eating or drinking of an effective amount of a saccharide containing 3-O-α-D-glucopyranosyl-D-glucose as a structural unit.

The effective amount of the above-mentioned saccharide means the same amount as the ingestion dose of the saccharide for the above-mentioned antistress agent.

The stress(es), to which the method for prevention or therapy of the present invention is applied, include especially stress(es) involved in decrease of cytokine production, stress(es) involved in apoptosis of immunocompetent cells, and the like, although all the phenomena in biologically strained states that are caused by stressors physiologically harmful to animals are encompassed.

The above-mentioned cytokine includes, for example, interleukins 1, 2, 3, 4, 5, 6, 7, 8, 9, 10, 11, 12, 13, 14, 15, 16, 17, 18, 19, 20, 21, 22, 23, 24, 25, 26 and 27, TNF (tumor necrosis factor)-α and -β, interferon-α, -β and -γ, and the like. The immunocompetent cells include B lymphocytes, T lymphocytes, mononuclear cells, macrophages, rod cells, and the like.

Furthermore, the secondary symptoms of chronic stress(es) include, circulatory system disorders (for example, oppression in the chest, palpitation, arrhythmia, etc.), digestive system disorders (for example, inappetence, stomachache, nausea, stomach ulcer, constipation and diarrhea), shoulder discomfort, headache, dizziness, anacatesthesia, asthenopia, systemic malaise, depression, and the like, besides reduction in infection-defense ability, delay of wound healing and metabolic disorders.

The method for prevention or therapy of the present invention remits the above-mentioned stress(es), suppresses decrease in cytokine production due to stress(es) and suppresses apoptosis of immunocompetent cells, thereby permitting to activate the host defense mechanisms and maintain the homeostasis in the living body.

The antistress agent of the present invention containing the composition comprising the saccharide containing 3-O-α-D-glucopyranosyl-D-glucose as a structural unit, for example the above-mentioned pharmaceutical preparation or the food or the beverage, can be packaged into a bottle, a plastic container, a paper container, a corrugated cardboard box or the like, or in combination thereof, by a per se known method. On said package, a description that the antistress agent can or should be used for stress(es) and/or for prevention or therapy of the secondary symptoms due to the stress(es) can be made, or a label of said description can be pasted, or a document of said description can be attached.

The present invention will be illustrated in more detail with reference to the following Examples, but is not restricted by these Examples.

Hereupon, the abbreviations used in the Examples are shown in the following:

PBS: Phosphate-buffered saline
ConA: Concanavalin A
PHA: Phytohemagglutinin
DEX: Dexamethasone
WST-1: 2-(4-Iodophenyl)-3-(4-nitrophenyl)-5-(2,4-disulfophenyl)-2H-tetrazolium monosodium salt
1-methoxy PMS: 1-Methoxy-5-methylphenazinium methylsulfate
IFN-γ: Interferon-γ
ELISA: Enzyme-linked immunosorbent assay
HRP: Horseradish peroxidase
IL-4: Interleukin-4
IL-10: Interleukin-10
IL-12: Interleukin-12
NK cells: Natural killer cells
DNA: Deoxyribonucleic acid
LPS: Lipopolysaccharide
TNF-α: Tumor necrosis factor-α

EXAMPLE 1

In this test, the effect of nigerose on suppression of the growth of human mononuclear cells due to DEX was verified.

After a blood sample obtained from a male adult was diluted two-fold with PBS, a Ficoll-Paque Plus solution (manufactured by Amersham Corporation) was added slowly to make double layers (blood diluted two-fold with PBS Ficoll-Paque Plus solution=4:3), which were centrifuged at the conditions of 400×g, 20° C. and 40 minutes. A mononuclear cell fraction present in the middle layer was recovered, and this mononuclear cell fraction washed twice with a 10-fold volume of PBS. The obtained mononuclear cells were suspended in an RPMI 1640 culture medium (manufactured by GIBCO BRL Corporation) to obtain a suspension of peripheral blood mononuclear cells. The number of cells in the suspension of peripheral blood mononuclear cells was measured with an automatic blood cell counter (manufactured by Sysmex Co., Ltd., Type CDA-500), and the mononuclear cells were suspended in RPMI 1640 culture medium so as to make the number of cells at a concentration of $2.0 \times 10^6$ cells/mL. This suspension was inoculated at 50 μL per one well on a 96-well tissue culture plate. To the inoculated suspension was added a solution of ConA or PHA in the RPMI 1640 culture medium in 50 μL per one well so as to make a final concentration of 2.0 μg/mL or 5.0 μg/mL, respectively. At the same time as the addition of ConA or PHA, solutions of DEX and nigerose in RPMI 1640 culture medium were added each in 50 μL per one well so as to make a final concentration of 10 nM and 0 μg/mL to 100 μg/mL, respectively. The mononuclear cells were incubated at 37° C. for 24 hours in a 5% $CO_2$ incubator. At 4 hours before completion of the incubation, a solution of WST-1 (manufactured by Dojindo Laboratories Inc.), dissolved in 0.4 mM 1-methoxy PMS (manufactured by Dojindo Laboratories Inc.) to make a concentration of 10 mM, was added in 10 μL per one well, and the absorbance at a measurement wavelength of 450 nm and a reference wavelength of 630 nm was measured at the time of completion of the incubation. The results were shown in Table 1.

TABLE 1

| DEX (nM) | Nigerose (μg/mL) | Absorbance (at 450 nm to 630 nm) | | | |
|---|---|---|---|---|---|
| | | ConA | | PHA | |
| | | 0 | 2.0 μg/mL | 0 | 5.0 μg/mL |
| 0 | 0 | 0.290 ± 0.002 | 0.303 ± 0.003 | 0.296 ± 0.010 | 0.322 ± 0.008 |
| 10 | 0 | — | 0.286 ± 0.004 | — | 0.299 ± 0.004 |
| 10 | 1 | — | 0.289 ± 0.004 | — | 0.290 ± 0.002 |
| 10 | 10 | — | 0.307 ± 0.003* | — | 0.305 ± 0.009 |
| 10 | 100 | — | 0.319 ± 0.004* | — | 0.319 ± 0.007* |

The symbol * means that "there is a significance" to the culture groups of 10 nM of DEX added and of 0 μg/mL of nigerose.

WST-1, when taken into living cells, is reduced by a intracellular mitochondrial dehydrogenase to produce water-soluble formazan. Because the amount of the thus-produced formazan is proportional to the number of the living cells, the measurement of the absorbance of formazan can be made as an index of the cell growth. As shown in Table 1, the growth of mononuclear cells induced by the addition of a cell stimulatory factor such as ConA and PHA was decreased by the addition of DEX, whereas the decrease in the growth of mononuclear cells due to DEX was significantly suppressed concentration-dependently by the addition of nigerose.

The mononuclear cells induced by stimulation of ConA and PHA include immune-related cells, for example, T cells and the like. The above-mentioned results indicate that the decrease in the growth of immune-related cells, for example, T cells and the like, due to the glucocorticoid which is continuously secreted at the time of stress(es), especially at the time of chronic stress(es) is/are suppressed by nigerose.

EXAMPLE 2

In this test, the effect of nigerose on the decrease in cytokine production due to DEX was verified.

(a) In a manner similar to that in Example 1, mononuclear cells were prepared from blood of a male adult, and the cultivation was initiated at a concentration of $5.0 \times 10^5$ mononuclear cells/mL. In a manner similar to that in Example 1, ConA or PHA as a cell stimulatory factor was added to the culture in 50 μL per one well so as to make a final concentration of 2.0 μg/mL or 5.0 μg/mL, respectively, thereby inducing cytokine production. At the same time as the addition of ConA or PHA, DEX and nigerose were added each in 50 μL per one well so as to make a final concentration of 10 nM and 0 μg/mL to 100 μg/mL, respectively, and the mononuclear cells were incubated at 37° C. for 24 hours in a 5% $CO_2$ incubator. After completion of the incubation, the amount of IFN-γ in the culture supernatant was measured by the ELISA. Table 2 showed the results.

The determination by the ELISA is shown in the following.

A 2 μg/mL solution of a mouse anti-human IFN-γ antibody (manufactured by Endogen Inc.) prepared in a borate buffer solution was added in 50 μL per one well on a 96-well ELISA plate, and the plate was allowed to stand at 4° C. for a day to adhere the mouse anti-human IFN-γ antibody to each well. The above-mentioned culture supernatant was added in 50 μL per one well on the ELISA plate adhering the mouse anti-human IFN-γ antibody, and the plate was allowed to stand at room temperature for 90 minutes, thereby binding the IFN-γ in the culture supernatant to the mouse anti-human IFN-γ antibody adhered on the plate. After washing the plate, a 0.5 μg/mL solution of a biotin-labeled mouse anti-human IFN-γ antibody (manufactured by Endogen Inc.) prepared in a borate buffer solution was added thereto in 100 μL per one well to bind to the IFN-γ bound with the mouse anti-human IFN-γ antibody adhered on the plate. After washing out an unbound biotin-labeled mouse anti-human IFN-γ antibody, a solution of Avidin-HRP (manufactured by BD PharMingen Inc.) diluted 1000-fold in a borate buffer solution was added thereto in 100 μL per one well to bind to the biotin-labeled mouse anti-human IFN-γ antibody bound with the IFN-γ. After washing out an excess of Avidin-HRP, a phosphate buffer solution containing 0.006 V/V % of hydrogen peroxide and 0.1 W/V % of orthophenylenediamine was added thereto in 100 μL per one well to allow to react at room temperature for 15 minutes, and then the reaction was stopped by addition of 1.5 N sulfuric acid. The absorbance at a measurement wavelength of 492 nm and a reference wavelength of 630 nm was measured, and the concentration of the IFN-γ in the culture supernatant was obtained from a calibration curve prepared with a recombinant IFN-γ.

TABLE 2

| DEX (nM) | Nigerose (μg/mL) | Amount of IFN-γ production (ng/mL) | | | |
|---|---|---|---|---|---|
| | | ConA | | PHA | |
| | | 0 | 2.0 μg/mL | 0 | 5.0 μg/mL |
| 0 | 0 | 0.029 ± 0.053 | 0.320 ± 0.070 | 0.081 ± 0.022 | 0.533 ± 0.095 |
| 10 | 0 | — | 0.106 ± 0.046 | — | 0.119 ± 0.022 |
| 10 | 1 | — | 0.075 ± 0.070 | — | 0.144 ± 0.022 |
| 10 | 10 | — | 0.136 ± 0.095 | — | 0.219 ± 0.095 |
| 10 | 100 | — | 0.365 ± 0.053* | — | 0.320 ± 0.038* |

The symbol * means that "there is a significance" to the culture groups of 10 nM of DEX added and of 0 μg/mL of nigerose.

(b) In a manner similar to that in Example 1, mononuclear cells were prepared from blood of a male adult, and the cultivation was initiated at a concentration of $5.0 \times 10^5$ mononuclear cells/mL in a manner similar to that in Example 1. To the culture was added a cell stimulatory factor, which was heated dead body cells of *Lactobacillus* plantarum L137, so as to make a final concentration of 1.0 μL. At the same time as the addition of *Lactobacillus* plantarum L137, DEX and nigerose were added each in 50 μL per one well so as to make a final concentration of 10 nM and 0 μg/mL to 100 μg/mL, respectively, and the mononuclear cells were cultivated at 37° C. for 24 hours in a 5% $CO_2$ incubator. After completion of the incubation, the amounts of IL-12 and IFN-γ in the culture supernatant were measured by the ELISA. The amount of IFN-γ was measured on the basis of the ELISA described in Example 2. The amount of IL-12 was measured in a manner similar to the ELISA described in Example 2, except that the IFN-γ in the ELISA described in Example 2 was replaced by IL-12. The results were shown in Table 3.

TABLE 3

| DEX (nM) | Nigerose (μg/mL) | IL-12 (ng/mL) *Lactobacillus plantarum* L137 | | IFN-γ (ng/mL) *Lactobacillus plantarum* L137 | |
|---|---|---|---|---|---|
| | | 0 | 1.0 μg/mL | 0 | 1.0 μg/mL |
| 0 | 0 | 0.016 ± 0.027 | 0.193 ± 0.062 | 0.125 ± 0.026 | 5.804 ± 1.175 |
| 10 | 0 | — | 0.121 ± 0.046 | — | 1.748 ± 0.307 |
| 10 | 0.1 | — | 0.093 ± 0.021 | — | 1.895 ± 0.816 |

TABLE 3-continued

| DEX (nM) | Nigerose (μg/mL) | IL-12 (ng/mL) Lactobacillus plantarum L137 | | IFN-γ (ng/mL) Lactobacillus plantarum L137 | |
|---|---|---|---|---|---|
| | | 0 | 1.0 μg/mL | 0 | 1.0 μg/mL |
| 10 | 1 | — | 0.130 ± 0.042 | — | 1.866 ± 0.890 |
| 10 | 10 | — | 0.171 ± 0.016* | — | 2.677 ± 1.000 |

The symbol * means that "there is a significance" to the culture groups of 10 nM of DEX added and of 0 μg/mL of nigerose.

As shown in Table 2 and Table 3, the IL-12 and the IFN-γ induced by the addition of the cell stimulatory factor was decreased by the addition of DEX, whereas the decrease of IL-12 and IFN-γ due to DEX was significantly suppressed concentration-dependently by the addition of nigerose.

The IL-12 is a cytokine involved in immunoregulatory functions such as activation of NK cells and the like, and the IFN-γ is also a cytokine that is produced in the body to protect the living body, when infected by a virus, and has an action to suppress the growth of the virus involved in immunity of leukocytes, lymphocytes, or the like. This fact is to indicate that the decrease in the production of IL-12 or IFN-γ, which is a cytokine involved in immunity, by the glucocorticoid secreted continuously at the time of stress(es), especially at the time of chronic stress(es), is suppressed by nigerose.

EXAMPLE 3

Effect of Nigerose on Activated Apoptosis

In a manner similar to that in Example 1, mononuclear cells were prepared from blood of a male adult, and the cultivation was initiated at a concentration of $5.0 \times 10^5$ mononuclear cells/mL in a manner similar to that in Example 1. To the culture was added ConA or a hemolytic *streptococcus* preparation OK-432 (picibanil, manufactured by Chugai Pharmaceutical Co., Ltd.) as a cell stimulatory factor, so as to make a final concentrations of 2.0 μg/mL or 1.0 μg/mL, respectively. At this time, nigerose was added to each of the culture groups so as to make a concentration of 1.0 μg/mL and 10 μg/mL, where a nigerose-free control group was provided to each of the culture groups. The mononuclear cells were incubated at 37° C. for 24 hours in a 5% $CO_2$ incubator. After completion of the incubation, apoptosis cells were fixed with an ssDNA Apoptosis ELISA kit (manufactured by Chemicon International, Inc.) which could specifically detect only the apoptosis cells, treated with a DNA-denaturing agent, then stained, and the absorbance (415 nm) was measured to quantify the degree of apoptosis. The results were shown in Table 4.

TABLE 4

| | | Absorbance (415 nm) | | |
|---|---|---|---|---|
| | | | Nigerose-added group | |
| | | Control group | 1.0 μg/mL | 10 μg/mL |
| Culture solution | | 1.143 ± 0.028 | 1.113 ± 0.053 | 1.134 ± 0.065 |
| Cell stimulatory factor | ConA | 1.718 ± 0.081 | 1.631 ± 0.175 | 1.372 ± 0.165* |
| | OK-432 | 1.800 ± 0.034 | 1.549 ± 0.276 | 1.767 ± 0.203 |

The symbol * means that "there is a significance" to the control group.

As shown in Table 4, a suppressive effect on the apoptosis was observed in the nigerose-added group.

This fact is to indicate the usefulness of nigerose against the apoptosis caused by the glucocorticoid secreted continuously at the time of stress(es), especially at the time of chronic stress(es). There is suggested the usefulness of nigerose especially in an aged person who is susceptible to the apoptosis due to stress(es).

EXAMPLE 4

Effect of nigerooligosaccharide on thymic and splenic atrophy due to DEX

Female BALB/c mice (8 weeks old) were divided into a group fed with a commercially available feed (control group) and a group fed with a commercially available feed mixed with a nigerooligosaccharide liquid sugar (Nigero S: content of nigerooligosaccharide: 30.8% by weight; manufactured by Takeda Food Products, Ltd.) at a concentration of 5% by weight (nigerooligosaccharide group). On one week of feeding, a half number of mice each in the control group and in the nigerooligosaccharide group was intraperitoneally administered with saline, and each of the remaining half number of mice was intraperitoneally administered with DEX (200 μg/mouse). After 24 hours of the administration, the thymus and spleen of each mouse were excised, and the weights of the excised thymus and spleen were measured. Table 5 shows the results.

TABLE 5

| | Weight of spleen (mg) | | Weight of thymus (mg) | |
|---|---|---|---|---|
| | Control group | Nigero-oligosaccharide group | Control group | Nigero-oligosaccharide group |
| physiological saline | 93.8 ± 11.7 | 98.2 ± 4.1 | 54.7 ± 6.8 | 54.9 ± 9.3 |
| DEX | 78.3 ± 19.3 | 92.6 ± 15.5 | 28.8 ± 10.3 | 33.2 ± 7.8 |

Each value shows the mean value ± the standard deviation in one group of 6 mice.

As shown in Table 5, in comparison with a significant decrease in the weights of spleen and thymus by the administration of DEX in the control group, the decrease in the weights of spleen and thymus due to DEX was suppressed in the mice in the nigerooligosaccharide group ingesting nigerooligosaccharide. This fact is to indicate that the nigerooligosaccharide is useful against the atrophy of immunocompetent organs due to the glucocorticoid secreted continuously at the time of stress(es), especially at the time of chronic stress(es).

EXAMPLE 5

Effect of Nigerooligosaccharide on Decrease in Cytokine Productivity Due to DEX

Before verifying the effect of nigerooligosaccharide, as a preliminary test in order to identify the decrease in cytokine productivity due to DEX, DEX (60 μg/mouse) was intraperitoneally administered to 14 weeks old, female BALB/c mice. Before and 24 hours after the administration of DEX, the spleen was excised from the BALB/c mice, and spleen cells were prepared by a conventional method. The prepared spleen cells were suspended in an RPMI 1640 culture medium so as to make a concentration of $5.0\times10^6$ cells/mL. This suspension was inoculated in 100 μL per one well on a 96-well tissue culture plate, and further a solution of a cell stimulatory factor, (1) PHA or (2) LPS, dissolved in the RPMI 1640 culture medium so as to make a final concentration of 12.5 μg/mL or 20 μg/mL, respectively, was added in 100 μL per one well. The spleen cells were cultivated at 37° C. for 24 hours in a 5% $CO_2$ incubator, and the concentrations of cytokines in the culture supernatant, IL-4 and IFN-γ for the foregoing (1) or IL-10 and TNF-α for the foregoing (2), were measured by the ELISA. The amount of IFN-γ was measured on the basis of the ELISA described in Example 2. The amounts of IL-4, IL-10 and TNF-α were measured in a manner similar to the ELISA described in Example 2, except that the IFN-γ in the ELISA described in Example 2 was replaced by IL-4, IL-10 or TNF-α. The results were shown in Table 6.

Hereupon, the cytokine production ratio (%) in the DEX-administered mice was calculated by the following equation:

Cytokine production ratio (%)=$(A/B)\times100$

A: The cytokine concentration in the culture supernatant of the cells of spleen excised 24 hours after the intraperitoneal administration of DEX B: The cytokine concentration in the culture supernatant of the cells of spleen excised before the intraperitoneal administration of DEX Table 6 shows the cytokine production ratio in the DEX-administered mice.

Next, in this test, to 14 weeks old, female BALB/c mice (6 mice per one group) was given as a drinking water ion-exchanged water or a 1 W/V % solution of a highly pure nigerooligosaccharide (19.8% by weight of nigerose, 36.5% by weight of a trisaccharide fraction mainly composed of nigerosylglucose, 40.2% by weight of a tetra- or more saccharide fraction mainly composed of nigerosylmaltose, and 3.5% by weight of glucose) in ion-exchanged water, and the mice were fed with a commercially available feed. On one week of feeding, DEX (60 μg/mouse) was intraperitoneally administered to the mice. After 24 hours of the administration, the spleen was excised, and spleen cells were cultivated at the same conditions as those in the preliminary test, and the concentrations of cytokines in the culture supernatant were measured. The measured values were shown in Table.

TABLE 6

| Cell stimu-latory factor | Cyto-kine | Preliminary test Cytokine production ratio (%) in DEX-administered mice | Final test DEX | Final test DEX + nigero-oligosaccharide |
|---|---|---|---|---|
| PHA | IL-4 | 65.8 | 2.1 ± 0.8 (pg/mL) | 3.8 ± 1.9 (pg/mL) |
|  | IFN-γ | 51.7 | 0.059 ± 0.027 (ng/mL) | 0.094 ± 0.023 (ng/mL) |
| LPS | IL-10 | 56.8 | 0.021 ± 0.011 (ng/mL) | 0.035 ± 0.004 (ng/mL) |
|  | TNF-α | 64.7 | 0.373 ± 0.062 (ng/mL) | 0.483 ± 0.124 (ng/mL) |

As shown in Table 6, it was confirmed in the preliminary test that the cytokine production ratio was significantly decreased by the administration of DEX. Under such conditions, it was indicated in the final test that the cytokine production ratio in the mice receiving the nigerooligosaccharide was evidently higher as compared with the control group. This fact is to indicate that the nigerooligosaccharide is useful against the reduction in the immune function due to the glucocorticoid secreted continuously at the time of stress(es), especially at the time of chronic stress(es).

INDUSTRIAL APPLICABILITY

Since the reduction in the immune function due to stress(es) can be suppressed according to the present invention, the antistress agent of the present invention is useful as a medicine, and also as a food or a beverage.

The invention claimed is:

1. A method for treatment of atrophy of thymus due to chronic stress, which comprises subjecting a mammal in which glucocorticoid is continuously secreted in response to chronic stress to eating or drinking of about 50 mg to 10 g per day of a nigerooligosaccharide wherein atrophy of thymus due to chronic stress is treated.

2. The method according to claim 1, wherein the nigerooligosaccharide is at least one kind of saccharide selected from the group consisting of nigerose, nigerosylglucose and nigerosylmaltose.

3. The method according to claim 1, wherein the nigelooligosaccharide is used as a food or beverage.

4. The method according to claim 3, wherein the food or beverage is selected from the group consisting of a nutritional supplementary food, a seasoning, a processed meat product, a processed marine product, a processed agricultural product, a staple, a seasoned food, a ready-to-eat food, a dessert, a milky oil product, a sweets and a snack.

5. The method according to claim 3, wherein the food or beverage is in the form selected from the group consisting of granule, tablet, dragee, chewing gum, candy, jerry and drink.

6. The method according to claim 3, wherein the food or beverage is in the form of syrup.

7. The method according to claim 1, wherein the mammal is human.

* * * * *

UNITED STATES PATENT AND TRADEMARK OFFICE
CERTIFICATE OF CORRECTION

| | | |
|---|---|---|
| PATENT NO. | : 7,786,093 B2 | |
| APPLICATION NO. | : 11/631618 | |
| DATED | : August 31, 2010 | |
| INVENTOR(S) | : Yoshitaka Hirose et al. | |

It is certified that error appears in the above-identified patent and that said Letters Patent is hereby corrected as shown below:

Title Page, Item (73) should read
-- (73) Assignee: House Wellness Foods Corporation,
Hyogo (JP) --.

Signed and Sealed this
Twenty-eighth Day of June, 2011

David J. Kappos
*Director of the United States Patent and Trademark Office*